United States Patent
Weinstrauch

(10) Patent No.: US 6,177,608 B1
(45) Date of Patent: *Jan. 23, 2001

(54) TAMPON

(75) Inventor: Fritz Weinstrauch, Kaarst (DE)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/765,846

(22) PCT Filed: Jun. 30, 1995

(86) PCT No.: PCT/EP95/02551

§ 371 Date: Jun. 26, 1997

§ 102(e) Date: Jun. 26, 1997

(87) PCT Pub. No.: WO96/00552

PCT Pub. Date: Jan. 11, 1996

(30) Foreign Application Priority Data

Jun. 30, 1994 (DE) .......................................... 94 10 595 U

(51) Int. Cl.$^7$ .................................................. A61F 13/15
(52) U.S. Cl. ............... 604/380; 604/385.17; 604/385.18; 604/904
(58) Field of Search .................................. 604/904, 358, 604/347, 378, 385.1, 285–289, 363, 379–380, 385.01, 385.17, 385.18

(56) References Cited

U.S. PATENT DOCUMENTS

| 2,336,257 | * | 9/1943 | Bailey | 604/907 |
|---|---|---|---|---|
| 2,499,414 | * | 3/1950 | Rabell | 604/907 |
| 3,834,389 | * | 9/1974 | Dulle | 604/907 |
| 3,946,737 | | 3/1976 | Kobler. | |
| 4,185,631 | | 1/1980 | McConnell. | |
| 4,211,225 | * | 7/1980 | Sibalis | 604/907 |
| 4,212,301 | * | 7/1980 | Johnson | 604/907 |
| 4,351,339 | | 9/1982 | Sneider. | |
| 4,553,965 | * | 11/1985 | Conn et al. | 604/907 |
| 5,498,252 | * | 3/1996 | Silber | 604/904 |

FOREIGN PATENT DOCUMENTS

| 565553 | | 8/1975 | (CH). | |
|---|---|---|---|---|
| 94 10 595 | | 6/1994 | (DE). | |
| 0146320 | * | 6/1985 | (EP) | 604/904 |
| 96/00552 | | 1/1996 | (WO). | |

OTHER PUBLICATIONS

Playtex Gentle Glide Applicator, copyright 1992.*

* cited by examiner

Primary Examiner—John G. Weiss
Assistant Examiner—K. M. Reichle
(74) Attorney, Agent, or Firm—Thomas J. Connelly; Jerry F. Janssen; Michael L. Winkelman

(57) ABSTRACT

A tampon for feminine hygiene having an absorbent core and a cover disposed around the core which is permeable to body fluids, the cover being provided with flexible barrier strips which are spreadable from the tampon surface. The barrier strips serve to close the space between the tampon surface and the walls of the vaginal duct when the tampon is inserted, preventing leakage especially in the time just after insertion. The barrier strips may be of either hydrophilic or hydrophobic material. In the embodiment in which the barrier strips are hydrophilic, they serve as absorbent elements of the tampon in addition to the tampon core. In the embodiment in which the barrier strips are of a hydrophobic material, they direct menstrual fluids inwardly to the absorbent tampon core. In yet another embodiment, the barrier strips may be of a folded two-layer construction filled with an absorbent material.

18 Claims, 5 Drawing Sheets

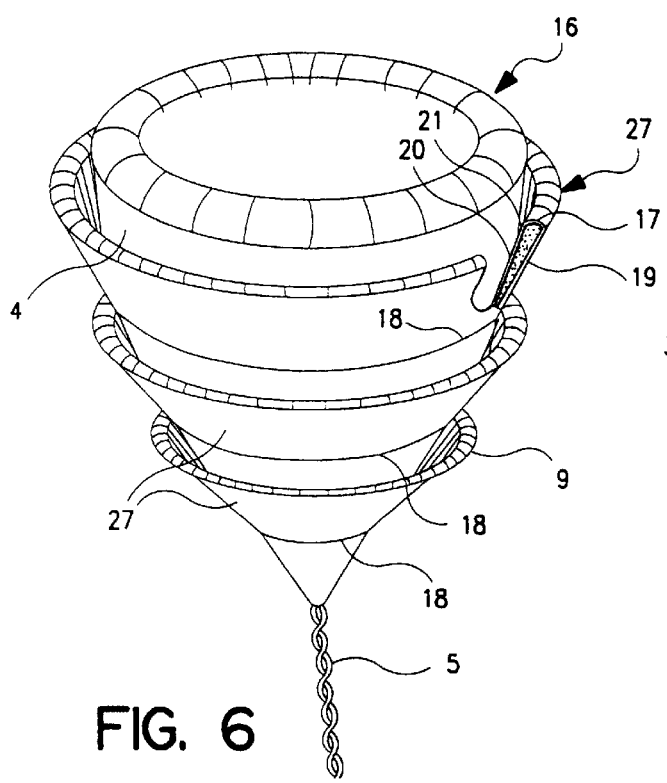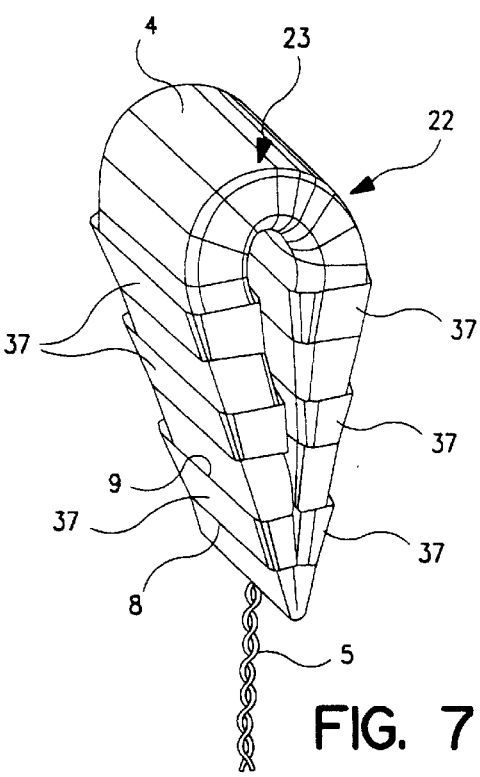

TAMPON

This application is a 371 of PCT/EP95/02551, filed Jun. 30, 1995, which claims priority from German patent application G9410595.2, filed Jun. 30, 1994.

TECHNICAL FIELD

The invention relates to a tampon, for feminine hygiene.

BACKGROUND

Various embodiments of tampons have been commonly used for a long time. Examples of tampons are wound-up tampons, so-called "tea bag tampons" or tampons manufactured from a non-woven web section.

Although tampons have been improved to a great extent with respect to the prevention of leakage and liquid absorption capacity, a basic problem associated with practically all kinds of tampons is the so-called "early leakage" problem, which means a failure of the tampon during the period of time shortly after its insertion. This is because in this state the tampon is not yet swollen by liquid absorption, so that it is not yet capable of fulfilling its function as a barrier to menstrual fluids in the vaginal duct. This is because free spaces remain around the tampon, allowing the passage of menstrual fluid.

SUMMARY OF THE INVENTION

In light of the problem described above, it is an object of the invention to provide a tampon with improved safety with respect to general failure and, in particular, to failure shortly after insertion of the tampon into the vaginal duct.

This object is achieved by the tampon according to the present invention which comprises an absorbent core and a cover, permeable to body fluids, disposed around the core, the cover being provided with at least one flexible barrier strip disposed laterally to the direction of insertion of the tampon, the barrier strip having first and second edges, the second edge being spaced apart from the first edge in the same direction as the direction of insertion of the tampon and being outwardly spreadable from the core at its second edge.

Further advantageous embodiments, features, aspects or details of the invention are evident from the dependent claims, the description and the drawings. The tampon according to the invention comprises barrier strips which spread from the tampon surface when the tampon is inserted into the vaginal duct and thereby close at least a major part of the free spaces between the tampon surface and the vaginal wall which are still present at that time.

Basically, these flexible barrier strips can extend in a longitudinal direction of the tampon at the surface thereof or in a helical configuration about the tampon. However, it is especially preferred for the barrier strips, for example in a wound-up tampon or bag tampon formed in a rotationally symmetrical manner, to extend in circumferential direction around the tampon and to be radially spreadable. Such barrier strips are particularly effective because they can reliably close the free spaces mentioned above between the tampon surface and the vaginal wall. Moreover as far as the ease of manufacture is concerned, such barrier strips extending in a circumferential direction are readily attachable to the tampon surface, which is especially advantageous in view of the fact that tampons are mass-produced articles.

One barrier strip variant which can be manufactured particularly efficiently is obtained by forming said strips from foldings of the cover material itself. Thus, in the machine for manufacturing, for instance a wound-up tampon, only a somewhat wider non-woven cover section needs to be fed via an appropriate folding means in order to provide a tampon according to the invention.

Preferably, the barrier strips can, of course, also be formed from separate strips attached to the cover by means of gluing, heat sealing, needle punching, embossing or the like.

The barrier strips of the tampon according to the invention can fulfill their safety function in different ways. For example, the barrier strips in their spread state can primarily act as a mechanical barrier and block the free spaces around the tampon mentioned above. In this connection, it is advantageous for the barrier strips to consist of a hydrophobic non-woven material because the resulting liquid-repellent effect causes an additional barrier effect.

Furthermore, the barrier strips can act as additional reservoirs for body fluids or as a means for conducting the body fluids toward the tampon surface. In this case, a hydrophilic finish of the non-woven material forming the barrier strips is advantageous.

The above-mentioned absorbent action of the barrier strips is further increased by means of a filling of absorbent material. A wadding band, wood pulp fluff or the like, for example, may be used as the absorbent material, which may in addition be supplemented by a so-called "superabsorbent", if desired.

By means of the permanent or releasable fixation of the second edges of the barrier strips of the tampon cover, the spreading behavior of the barrier strips can be controlled. These fixations allow bags to be formed by the barrier strips at the outer side of the tampon, said bags being capable of retaining, for example, solids in the menstrual fluid particularly effectively.

DETAILED DESCRIPTION OF THE DRAWING FIGS.

Further features, details and advantages of the invention are evident from the following description, wherein embodiments of the subject matter of the invention are explained in greater detail by means of the enclosed drawings, wherein:

FIGS. 6 and 7 are two further embodiments of tampons according to the invention.

DETAILED DESCRIPTION

Figure 1:
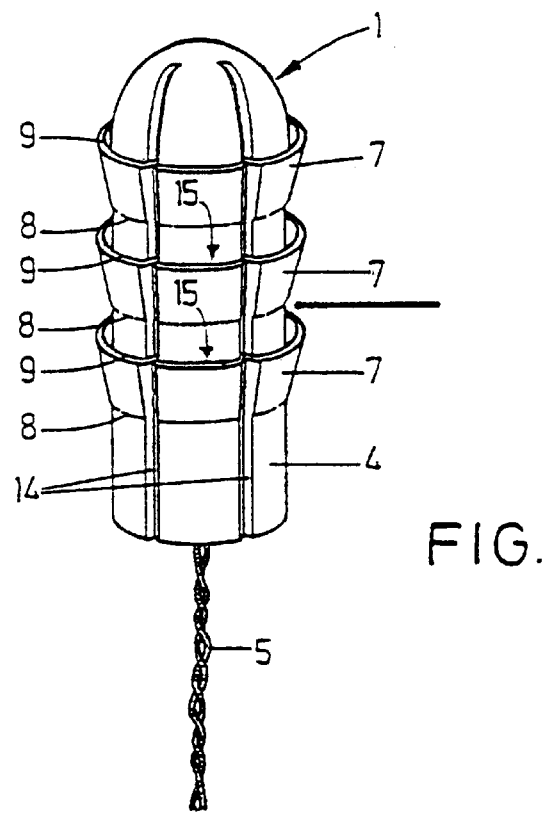
FIG. 1 is a perspective view of a wound-up tampon.

The basic construction of the wound-up tampon shown in FIG. 1 corresponds to conventional wound-up tampons, i.e., the tampon 1 comprises an absorbent core of a wadding band 2 wrapped on itself (FIGS. 3 to 5), around which a cover 4 formed of a non-woven strip 3 (FIGS. 3 to 5) is wrapped. Furthermore, a withdrawal string 5 connected to the core is provided at the end of the wound-up tampon 1 opposite to the rounded tip 6.

In the embodiment shown in FIG. 1 the cover 4 is provided with three barrier strips 7 which are distributed over the length thereof and extend around the wound-up tampon 1 in a circumferential direction thereof, the first edge 8 of said barrier strips, which are disposed opposite to the insertion direction E of the wound-up tampon 1 extend in a circumferential direction, and merge integrally with cover 4 in a manner which will be described hereinafter in greater detail. The barrier strip 7 is loose up to its opposite or second edge 9 disposed towards the insertion direction E, which allows the barrier strips 7 to spread from the tampon surface 24 as shown in FIG. 2.

Figure 2:
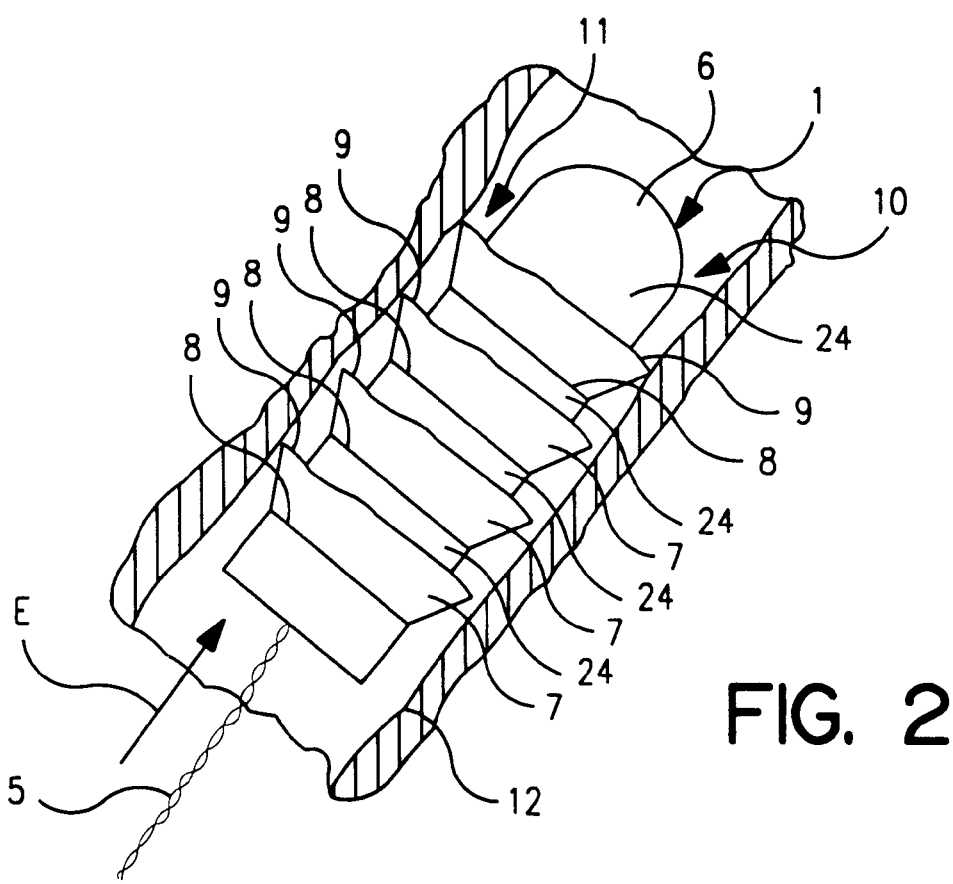
FIG. 2 is a schematic view of the tampon according to FIG. 1 in use.

This is schematically shown in FIG. 2. As can be seen, the barrier strips 7 spread radially outwardly when the wound-up tampon 1 is inserted into the vaginal duct 10 and close the free space 11 between the outer surface of the wound-up tampon 1 and the vaginal wall 12. As a result, the barrier strips 7 form a mechanical barrier against the passage of menstrual fluid through said free space 11, on the one hand. On the other hand, the barrier strips 7 themselves absorb menstrual fluid, because they can be made of a hydrophilic, absorbent material, for example. Not least, the barrier strips 7 conduct the menstrual fluid towards the tampon surface, thus allowing the tampon to absorb fluid more rapidly and thus to swell.

Figure 5:
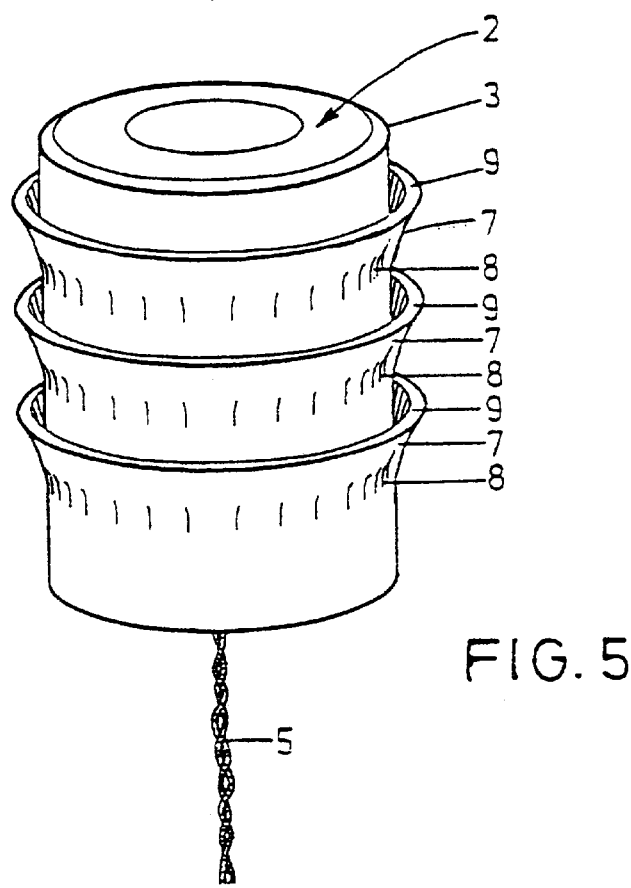
FIGS. 3 to 5 are perspective views of intermediate steps of the manufacture of a tampon according to FIG. 1.
Figure 3:
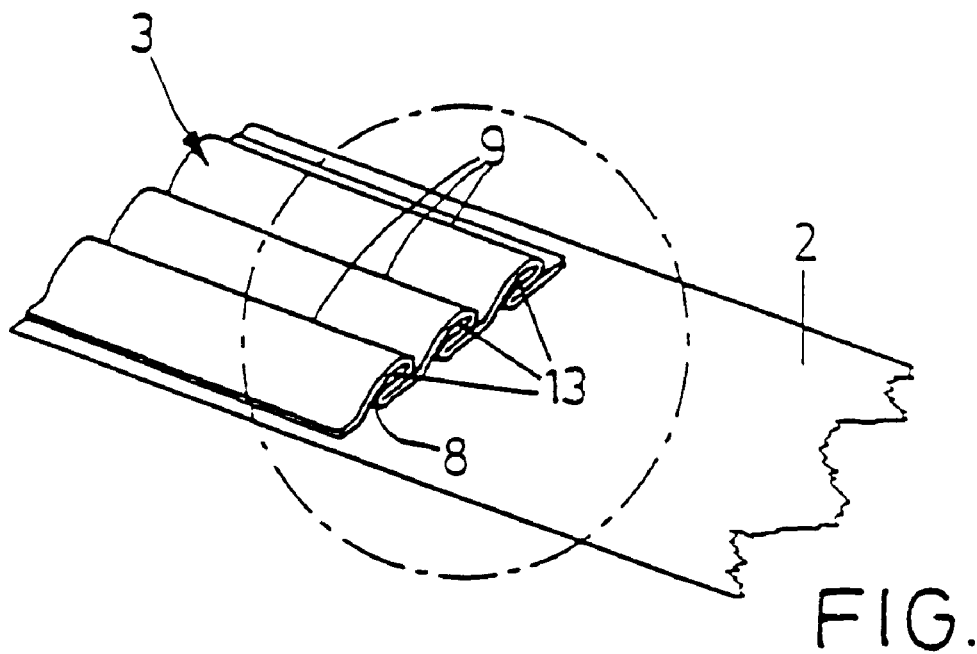
Figure 4:
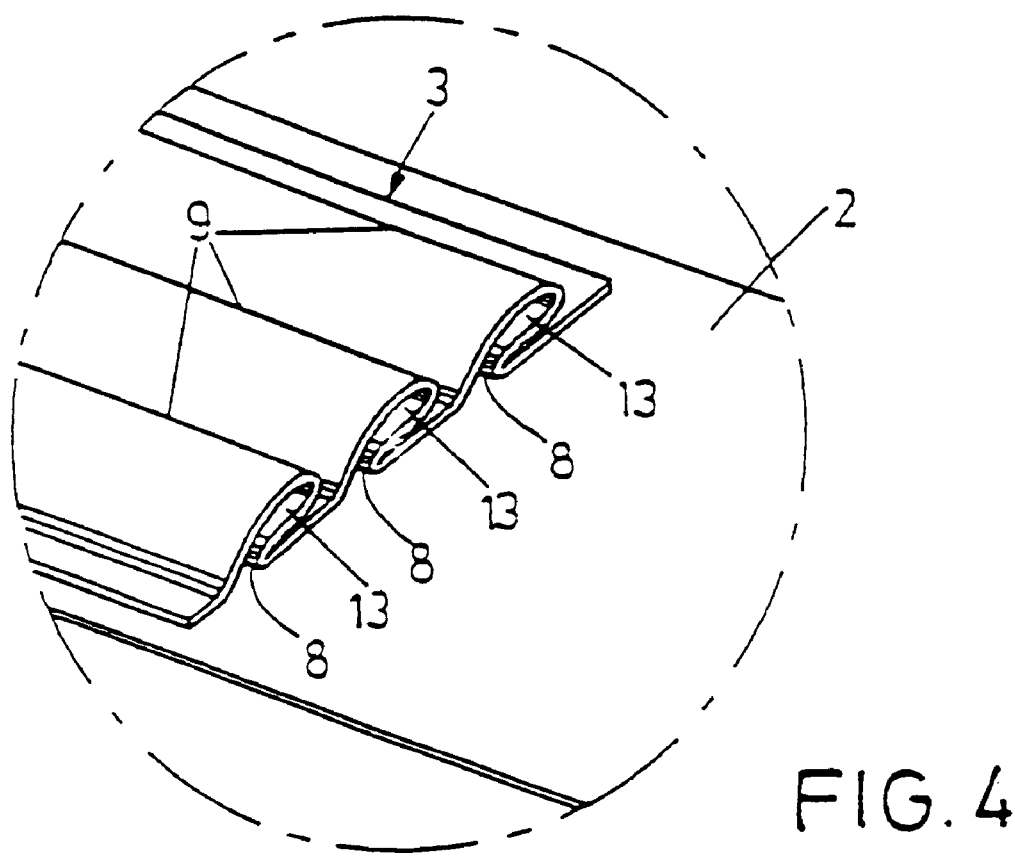

As is evident from FIGS. 3 to 5, the barrier strips 7 of the wound-up tampon 1 shown in FIG. 1 are formed from foldings of the cover material, because during manufacture the non-woven fabric strip 3 forming cover 4 of the tampon is attached in the form of foldings or pleats 13 to the wadding band 2 forming the core. The pleats extend in a longitudinal direction of the wadding band 2 and the non-woven strip 3, so that, after the wadding band 2 and the non-woven fabric strip 3 have been wound up, the barrier strips 7 extend around the tampon in a circumferential direction (FIG. 5).

After the wadding band 2 and the non-woven fabric strip 3 (laid into pleats 13) have been wound up, the latter is fixed on itself in conventional manner, for example, by means of hot embossing. As a result, the tampon blank shown in FIG. 5, is obtained. This tampon blank is pressed in a pressing tool into the shape shown in FIG. 1 in a conventional manner, at the same time forming spaced apart sections or grooves 14 extending in a longitudinal direction of the wound-up tampon 1 being embossed as well due to the pressing tool being of corresponding shape. As a result of these grooves 14, distributed over the circumference of the wound-up tampon 1, the second edges 9 of the barrier strips 7 are in addition fixed to the tampon cover 4 in the area of the embossed grooves; this fixation can be a permanent one or only a temporary one, depending on how intensively the grooves are embossed. This fixation causes bags 15 to be formed between the grooves 14 in the area of the barrier strips 7.

FIG. 6 shows a so-called bag tampon 16, the basic construction of which is also common and thus does not have to be described in greater detail. Again, barrier strips 27 extending around the tampon body in circumferential direction are arranged at cover 4 of the conical tampon body, said cover 4 being filled with absorbent material (for example wood pulp fluff). In contrast to the wound-up tampon according to FIG. 1, the barrier strips 27 of this embodiment are formed by non-woven strips 17 which are initially separate from cover 4 and which, during manufacture, are folded on themselves and glued together and to said cover 4 in the area of their free edges 18 disposed opposite to the insertion direction E. The space between the two layers 19, 20 of the barrier strip 27 is filled with an absorbent material (for example, wood pulp fluff 21). The non-woven strips 17 per se may consist, for example, of a hydrophilically finished polypropylene spun-bonded non-woven fabric. However, any other non-woven materials commonly used in manufacturing tampons can be used as well.

Figure 8:
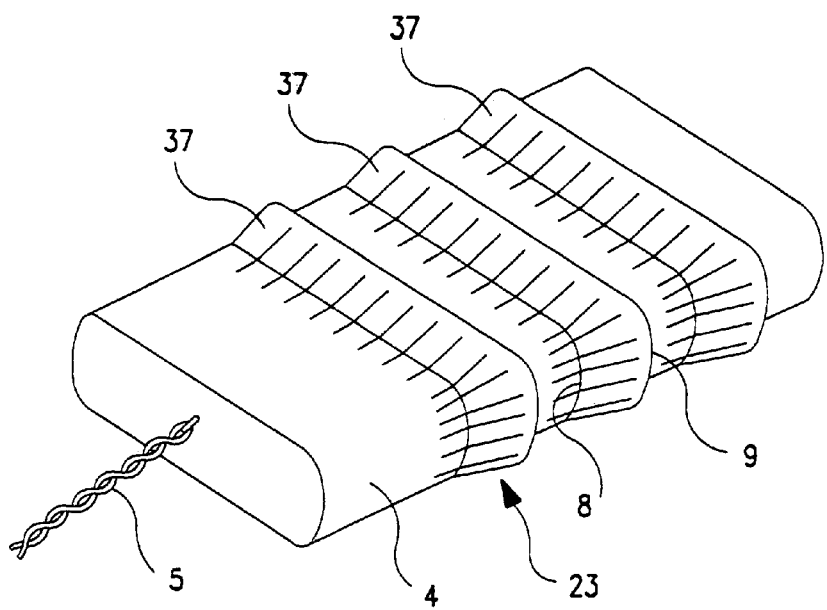
FIG. 8 is a perspective view of the tampon according to FIG. 7 in an intermediate manufacturing step.

As a further embodiment of the invention, FIG. 7 shows a tampon 22 consisting of a U-shaped, right-parallelopiped tampon body 23 which is folded on itself. The latter is commonly made of an absorbent core (not shown) and a cover 4. In this embodiment the core is formed from a non-woven band laid into a layer package. Again, the cover comprises barrier strips 37 integrally joined thereto by means of appropriate folding, said barrier strips 37 extending around the tampon blank partially shown in FIG. 8.

Figure 9:
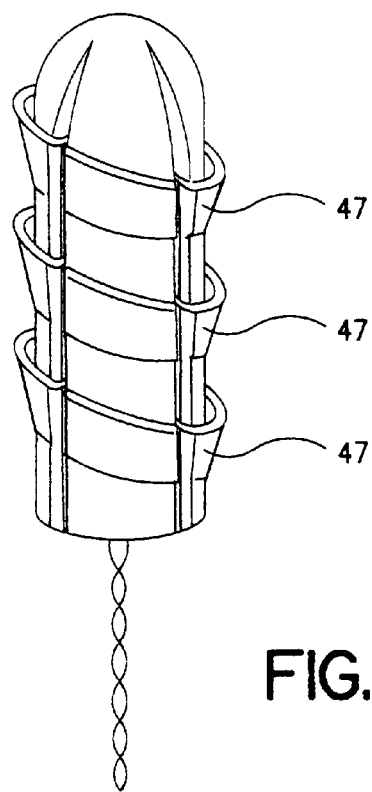
FIG. 9 is a perpective view of a spirally wound-up tampon.

FIG. 9 is an alternate embodiment similar to FIG. 1, except that the barrier strips 47 are wound-up in a spiral or helical manner.

In general, the height between the first edge and the second edge of the barrier strips 7, 27, 37 or 47 shown in the various embodiments of FIGS. 1, 6, 7 and 9 can be approximately 5 mm up to a maximum of 25 mm. The number of barrier strips can vary between 1 and preferably approximately 5.

What is claimed is:

1. A tampon for feminine hygiene comprising an absorbent core, a cover which is disposed around the core so as to define a tampon surface and is permeable to body fluids, the tampon being further provided with at least one flexible barrier strip disposed around the tampon surface laterally to a direction of insertion of the tampon, the at least one barrier strip having first and second edges, the first edge attached at the tampon surface the second edge being spaced apart from the first edge in the same direction as the direction of insertion of the tampon, the barrier strip being outwardly spreadable from the tampon surface at the second edge of thereof.

2. A tampon according to claim 1 further comprising a withdrawal string attached to the core of the tampon.

3. A tampon according to claim 1 wherein the at least one barrier strip is formed of a hydrophilic non-woven fabric.

4. A tampon according to claim 1 wherein the at least one barrier strip is formed of a hydrophobic non-woven fabric.

5. A tampon according to claim 1 wherein the at least one barrier strip is integral with, and forms a part of, the cover.

6. A tampon according to claim 5 wherein the at least one barrier strip is a pleat formed by a fold in the cover of the tampon.

7. A tampon according to claim 6 wherein the pleat is filled with an absorbent material.

8. A tampon according to claim 1 wherein said at least one barrier strip is initially separate from the cover of the tampon prior to attachment to the tampon cover.

9. A tampon according to claim 8 where the at least one barrier strip is attached at its first edge to the tampon cover by one of gluing, heat sealing, needle punching, and embossing.

10. A tampon according to claim 1 wherein the second edge of the at least one barrier strip is temporarily fixed to the tampon core at spaced apart locations around the circumference of the tampon core to form bags, each bag having a bag opening between the at least one barrier strip second edge and the cover between the spaced apart locations.

11. A tampon according to claim 1 wherein the second edge of the at least one barrier strip is permanently fixed to the tampon core at spaced apart locations around the circumference of the tampon core to form bags, each bag having a bag opening between the at least one barrier strip second edge and the cover between the spaced apart locations.

12. A tampon according to claim 1 wherein the at least one flexible barrier strip is from two to five flexible barrier strips.

13. A tampon according to claim 1 wherein the distance between the first and second edges of the barrier strip is between about 5 mm and 25 mm.

14. A rotationally symmetrical tampon for feminine hygiene comprising an absorbent core and a cover surrounding the core so as to define a tampon surface, the cover being provided with at least one barrier strip extending circumferentially around the tampon surface, the at least one barrier strip having first and second edges, the second edge being spaced apart from the first edge in the same direction as a direction of insertion of the tampon, the at least one barrier strip being radially outwardly spreadable from the tampon surface.

15. A tampon according to claim 14 having a substantially cylindrical shape.

16. A substantially cylindrically-shaped tampon for feminine hygiene comprising an absorbent core and a cover surrounding the core, the cover being provided with at least one barrier strip disposed circumferentially around the core, the at least one barrier strip having first and second edges, the first edge of the at least one barrier strip being attached to the core of the tampon and the second edge of the at least one barrier strip being attached to the core of the tampon at spaced apart locations about the circumference thereof, the second edge being spaced apart from the first edge in the same direction as a direction of insertion of the tampon, the at least one barrier strip being outwardly spreadable from the core of the tampon at the second edge of thereof between the spaced apart attached locations to define bags, each bag having a bag opening between the cover and the at least barrier strip second edge for receiving menstrual fluids and solids.

17. A tampon according to claim 16 wherein the spaced apart attached locations of the second edge of the at least one barrier strip extend longitudinally along the tampon.

18. A tampon according to claim 16 wherein the spaced apart attached locations comprise grooves embossed in the tampon.

* * * * *